United States Patent [19]

Kao et al.

[11] Patent Number: 4,696,814
[45] Date of Patent: Sep. 29, 1987

[54] PARENTERAL PHENYTOIN COMPOSITIONS

[75] Inventors: Shui-Hsi Kao; Allen I. Kay, both of Succasunna; Karla Sampson, West Caldwell, all of N.J.

[73] Assignee: Warner-Lambert Company, Morris Plains, N.J.

[21] Appl. No.: 767,997

[22] Filed: Aug. 21, 1985

[51] Int. Cl.$^4$ .................. A61K 31/79; A61K 31/415
[52] U.S. Cl. ...................................... 424/80; 514/398
[58] Field of Search .......................... 424/80; 514/398

[56] References Cited

PUBLICATIONS

Chem. Abst., 90-76468n (1979).
Chem. Abst., 92-135314a (1980).
Chem. Abst., 101-157567s (1984).

Primary Examiner—Stanley J. Friedman
Attorney, Agent, or Firm—Ronald A. Daignault

[57] ABSTRACT

Stable, aqueous solutions of phenytoin sodium can be made using polyvinylpyrrolidone with or without an alcoholic solvent system.

12 Claims, No Drawings

PARENTERAL PHENYTOIN COMPOSITIONS

BACKGROUND

Phenytoin is 5,5-diphenyl-2,4-imidazolidinedione. It is a well-known pharmaceutical agent having anticonvulsant and antiepileptic activity. Its preparation is described in U.S. Pat. No. 2,409,754.

Due to phenytoin's poor solubility in water, phenytoin sodium is employed in the preparation of injectable solutions of the drug. In order to stabilize solutions of phenytoin sodium, it is conventional to employ aqueous alcoholic solvent systems. Such solvent systems generally contain propylene glycol and/or other alcohols.

Even in the presence of alcoholic solvents, these solutions are unstable following dilution in intravenous fluids in that crystals form therein, precluding their safe use.

Thus, the need arose for stable aqueous preparation based on phenytoin, with or without solvents, which can be used in combination with one or more conventional intravenous fluid(s).

THE INVENTION

It has been discovered that aqueous solutions of phenytoin sodium can be stabilized against undesirable crystal formation by the addition of suitable amounts of polyvinylpyrrolidone (PVP). The use of alcoholic solvent systems along with PVP is optional.

In a preferred embodiment, 50 mg/ml aqueous phenytoin sodium is mixed with about 3-17% PVP.

Weight percentages are based on total compensation weight, unless abated otherwise.

Optionally, about 40 wt. % propylene glycol and about 10 wt. % ethyl alcohol can be added to the PVP-containing mixture.

The pH of the final solution to be subsequently diluted with I.V. fluid such as 0.9% sodium chloride injection or 5% dextrose injection should be in the range of about 10 to about 13, preferably about pH 12.

OBJECTS OF THE INVENTION

It is an object of the invention to provide novel aqueous solutions of phenytoin sodium.

It is a further object to provide preparations for the administration of phenytoin sodium which contain these novel solutions.

It is yet another object to provide a method of making stabilized solutions of phenytoin sodium.

It is still another object to provide a method for administering an anti-convulsant comprising the administration of a material containing phenytoin sodium and PVP in a weight ratio of about 1:0.5 to about 1:3.5.

ADVANTAGES OF THE INVENTION

The solutions, preparations and materials made in accordance with this invention generally exhibit several advantages which conventional phenytoin and phenytoin sodium-containing substances do not.

Phenytoin, because of its low solubility, cannot be effectively used in injectable solutions. It is extremely difficult to ensure uniform dosages when it is used alone in aqueous solutions.

Phenytoin sodium, on the other hand, is more soluble in water, but it rapidly dissociates into phenytoin, which then comes out of solution, resulting in precipitation especially during intravenous infusion. The preparations and methods set forth in the invention have neither the low solubility of phenytoin nor the crystals formation usually associated with the conventional solutions of phenytoin sodium.

The high solubility of the phenytoin sodium/PVP combinations in water makes parenteral formulations containing them highly useful. For example, they can be diluted with suitable fluid(s) to make preparations suitable for intravenous infusion.

Other objects and advantages of the invention will become apparent after a consideration of the following description.

DESCRIPTION OF THE INVENTION

Phenytoin and phenytoin sodium are well-known compounds. They are described in *The Merck Index*, 10th ed. (1983) on pages 1054 and 1055.

The invention is concerned with novel solutions which result from the combining of phenytoin sodium with PVP in aqueous environments.

By "aqueous environment" is meant water-containing systems which optionally include conventional diluents for phenytoin sodium. Such conventional diluents include alcoholic solvents, such as $C_{1-5}$ alcohols, $C_{2-6}$ diols, and the like. Ethanol and propylene glycol are preferred alcohols. Mixtures are contemplated.

While alcoholic solvents are preferred, other diluents may be incorporated in the compositions so long as they do not detract from the solubility or stability of the phenytoin sodium.

Generally, the phenytoin sodium and PVP components will be brought together in aqueous solution. Preferred methods for preparing the combinations include:

(1) dissolving dry PVP into phenytoin sodium in aqueous solution;

(2) mixing aqueous PVP solutions with aqueous phenytoin sodium solution; and (3) dry mixing of PVP and phenytoin sodium, followed by solution in aqueous medium. Other conventional solution techniques can be employed.

The PVP/phenytoin sodium solutions are suitable for dilution with other fluids to render them useful for intravenous infusion.

The pH of the solutions will range from about 10 to about 13, with a pH of 12 preferred.

The quantity of phenytoin sodium in these solutions will range from about 1 to about 10 wt. %, and preferably about 4 to about 5 wt. % based on the weight of the total composition (i.e., PVP, water, and phenytoin sodium).

The quantity of PVP in these solutions will range from about 3 to about 17 wt. %, and preferably about 6 to about 10 wt. %, based on the total composition weight.

In general, the weight ratio of phenytoin sodium to PVP in these solutions and in the preparations subsequently produced therefrom will be about 1:0.5 to about 1:3.5, with about 1:2 preferred.

When a diol solvent, such as propylene glycol is present it will usually be used in an amount between about 20 to about 80 wt. %, and preferably about 40 wt. %.

When an alcohol solvent is used, e.g., ethanol, it will generally be present at about 5 to about 15 wt. %, and preferably about 10 wt. %, based on total composition weight.

Thus the weight ratio of diol to alcohol solvent components, when both are used will generally be about 1:0.25 to about 1:0.75.

The composition of the invention—i.e., the combinations of phenytoin sodium, PVP, and optional alcoholic solvents—can be subjected to conventional purification, e.g., sterilization procedures. They may then be suitably packaged for storage and/or use, e.g., in ampoules, vials, syringes.

In order to adjust the pH of the compositions to the proper value, sodium hydroxide or other suitable alkaline material(s) is generally added thereto. If the solutions' pH exceeds the useful values, it can be lowered via the additional of hydrochloric acid or other suitable acidic substance(s).

The intravenous fluids with which the compositions of the inventions are usually mixed include conventional fluids whose properties do not detract from the solubility of the phenytoin sodium or the polyvinylpyrrolidone components. In general, they are aqueous solutions containing conventional quantities of electrolytes, nutrient, and the like.

While these diluents are generally referred to as aqueous, they may contain as their principal constituents non-aqueous media, so long as those media are pharmaceutically acceptable and do not interfere with the solubility of the phenytoin sodium ingredient.

Useful intravenous fluids include aqueous solutions of saline and dextrose. Preferred saline solutions contain up to 0.9%, preferably 0.9 wt. %, sodium chloride in aqueous, preferably water, solution.

Useful dextrose solutions are those containing about 1 to about 10 wt. %, preferably 5 wt. %, dextrose in aqueous, preferably water, solution.

The combining of the phenytoin sodium/PVP compositions with conventional fluids to make preparations suitable for administration via injection is effected by conventional methods. Simple mixing of the compositions with suitable quantities of the fluids is a preferred technique.

EXAMPLE I 750 ml of water for injection, USP was heated to 40°–45° C. in a water bath. 100.0 g. polyvinylpyrrolidone, USP was added with vigorous mixing, until dissolved. The solution was cooled to room temperature in an ice water bath.

10 ml of 1.0N aqueous NaOH solution was added and mixed well. 50.0 g phenytoin sodium USP (adjusted to 100% purity based on assay) was added and mixed well. If necessary, the pH of this mixture can be adjusted at this point with NaOH to a pH of about 12.1–12.3, preferably 12.2. A sufficient amount of water for injection was added to yield 980 ml. Mixing is continued. pH may again be adjusted, if necessary, to pH 12.20 with NaOH solution.

Enough water for injection was added, with mixing, to bring the volume to 1000 ml.

The solution was sterilized by filtration through a previously sterilized Millipore assembly fitted with a Pall N66R membrane using nitrogen for positive pressure. 5.3–5.5 ml of the solution was aseptically filled under nitrogen atmosphere into previously sterilized and depyrogenated ampoules. The ampoules were post-purged with high purity nitrogen. The ampoules were sealed.

The resultant solution was a light yellow clear solution having a tentative pH of 12.1–12.3. It is stable for at least three months in ampoules.

It is highly preferred that, as precautions, the solutions be kept out of contact with $CO_2$. In addition, maintenance of the solution under nitrogen during preparation, filling and storage is highly desirable.

EXAMPLE II 50 g of phenytoin sodium USP (adjusted to 100% purity based on assay) was mixed with about 275 ml of water for injection, USP. To this mixture was added 30.4 ml of 0.84% aqueous sodium hydroxide solution (made by combining 1.68 g NaOH with 200 ml water for injection, USP). A slurry was produced.

To the slurry was added 400.0 ml propylene glycol, USP and 110.4 ml ethanol USP (5.0% excess of alcohol was included). Mixing was continued until a clear solution was formed. Polyvinylpyrrolidone, USP, was then added with vigorous mixing, until dissolved.

Any pH adjustment, if necessary, can be made by adding NaOH to give a pH of about 12.

A sufficient amount of water for injection was added to bring the volume to 1,000 ml. The ingredients were mixed well.

The solution was sterilized by filtration through a previously sterilized Millipore assembly fitted with a Pall N66R membrane using nitrogen for positive pressure. Previously sterilized and depyrogenated ampoules were aseptically filled under a nitrogen atmosphere with 5.1–5.3 ml of the solution. The ampoules were post-purged with high purity nitrogen. The ampoules were sealed.

The final composition was a light yellow clear solution having a tentative pH of about 12.1 to 12.3, preferably 12.2. It was stored in Kimble 5 cc Type I treated ampoules.

It is stable for at least three months in ampoules and at least one month in vials.

The solutions produced in Example I are exemplary of solutions which can be produced using various concentrations of polyvinylpyrrolidone (PVP) in a wholly aqueous system containing sodium hydroxide at a pH of about 12.0. Since they are totally aqueous systems, they can be used for direct IV push at any rate the physician desires based on patients' needs.

In addition, the solutions produced in Examples I and II exhibit sufficient physical stability following dilution in either 5% Dextrose Injection, USP or 0.9% Sodium Chloride Injection, USP, to allow for the safe use of this product for IV infusion.

Reasonable variations, such as those which would occur to a skilled artisan, can be made herein without departing from the scope of the invention.

We claim:

1. An injectable composition containing a mixture of about 1–10 wt % phenytoin sodium and about 3 to about 17 wt % polyvinylpyrrolidone and having a pH of about 10 to about 12.3.

2. An aqueous preparation comprising the composition of claim 1 and further comprising at least one intravenous fluid.

3. The preparation of claim 2 wherein the intravenous fluid is saline solution.

4. The preparation of claim 2 wherein the intravenous fluid is dextrose solution.

5. The composition of claim 1 further comprising at least one alcoholic solvent selected from the group consisting of: propylene glycol and ethanol.

6. The preparation of claim 3 further comprising at least one alcoholic solvent selected from the group consisting of propylene glycol and ethanol.

7. The preparation of claim 4 further comprising at least one alcoholic solvent selected from the group consisting of propylene glycol and ethanol.

8. The composition of claim 1 further comprising an alkaline material.

9. The composition of claim 8 wherein the alkaline material is sodium hydroxide.

10. The composition of claim 9 further comprising an alkaline material.

11. The composition of claim 10 wherein the alkaline material is sodium hydroxide.

12. The composition of claim 11 wherein both propylene glycol and ethanol are present.

* * * * *